United States Patent [19]
Castor et al.

[11] Patent Number: 5,380,826
[45] Date of Patent: Jan. 10, 1995

[54] SUPERCRITICAL FLUID DISRUPTION OF AND EXTRACTION FROM MICROBIAL CELLS

[75] Inventors: Trevor P. Castor, Arlington; Glenn T. Hong, Tewksbury, both of Mass.

[73] Assignee: Aphios Corporation, Woburn, Mass.

[21] Appl. No.: 953,183

[22] Filed: Sep. 29, 1992

Related U.S. Application Data

[63] Continuation of Ser. No. 799,767, Nov. 27, 1991, abandoned, which is a continuation of Ser. No. 680,610, Apr. 1, 1991, abandoned, which is a continuation of Ser. No. 382,858, Jul. 20, 1989, abandoned.

[51] Int. Cl.$^6$ .......................... C07K 3/12; C07K 1/14; C12P 19/34; C12P 21/00

[52] U.S. Cl. .................... 530/422; 435/270; 435/91.1; 435/71.1; 435/71.2; 530/423; 530/426; 536/25.41; 554/8

[58] Field of Search .................. 435/272, 270, 816, 4, 435/71.1, 71.2, 91; 436/148; 554/8; 530/422, 423, 426; 536/25.41

[56] References Cited

U.S. PATENT DOCUMENTS

| | | | |
|---|---|---|---|
| 2,190,689 | 2/1940 | Torrington | 195/66 |
| 3,458,139 | 7/1969 | Edebo | 241/1 |
| 3,556,414 | 1/1971 | Eberty, Jr. | 241/1 |
| 3,605,843 | 9/1971 | Dean, Jr. et al. | 146/223 |
| 3,880,066 | 4/1975 | Ruget | 99/468 |
| 3,887,144 | 6/1975 | Schaeffer | 241/301 |
| 4,084,757 | 4/1978 | Rakitin et al. | 241/301 |
| 4,255,458 | 3/1981 | Roselius et al. | 426/424 |
| 4,280,961 | 7/1981 | Schneider et al. | 260/412.8 |
| 4,331,695 | 5/1982 | Zosel | 426/430 |
| 4,446,923 | 8/1984 | Friedrich | 260/412.4 |
| 4,476,225 | 10/1984 | Grigorian et al. | 435/287 |
| 4,495,207 | 1/1985 | Christianson et al. | 426/312 |
| 4,591,505 | 5/1986 | Prince | 424/101 |
| 4,680,262 | 7/1987 | Bechner et al. | 435/68 |
| 4,714,591 | 12/1987 | Avedesian | 422/140 |
| 4,749,522 | 6/1988 | Kamarei | 554/8 |
| 4,749,783 | 6/1988 | Jordan et al. | 530/393 |
| 4,753,788 | 6/1988 | Gamble | 424/264 |
| 4,764,369 | 8/1988 | Neurath et al. | 424/89 |
| 4,833,165 | 5/1989 | Louderback | 514/694 |
| 4,876,241 | 10/1989 | Feldman et al. | 541/2 |
| 4,879,114 | 11/1989 | Catsimpoolas | 424/95 |
| 4,939,176 | 7/1990 | Seng et al. | 514/724 |

FOREIGN PATENT DOCUMENTS

| | | |
|---|---|---|
| 214145 | 10/1984 | German Dem. Rep. |
| 59-140299 | 8/1984 | Japan |
| 2697 | 5/1987 | WIPO |

OTHER PUBLICATIONS

Lin, Ho–Mu, Disintegration of Yeast Cells by Pressurized Carbon Dioxide, Biotechnol Prog 1991, 7, pp. 201–204.

Fraser, D., "Bursting Bacteria by Release of Gas Pressure," Nature, vol. 1:33–34 (Jan. 6, 1951).

Kamihira et al., "Sterilization of Microorganisms with Supercritical Carbon Dioxide," Agric. Biol. Chem., 51 (2):407–412 (1987).

Taniguchi et al., "Brewing of Sake from Rice and Rice-Koji Defated by Supercritical Carbon Dioxide Treatment," J. Ferment, Technol., vol. 65, No. 2, 211–214 (1987).

Lin et al., "Disintegration of Yeast Cells by Pressurized Carbon Dioxide," Biotechnol. Prog. vol. 7:201–204 (1991).

Lin, et al., "An Improved Method for Disruption of Microbial Cells with Pressurized Carbon Dioxide," Biotechnol Prog 8:165–166 (1992).

Foster et al., "Rupture of Bacteria by Explosive Decompression," J. Bacteriol. 83:330–334 (1962).

*Primary Examiner*—Jeffrey E. Russel
*Assistant Examiner*—Ralph Gitomer
*Attorney, Agent, or Firm*—Wolf, Greenfield & Sacks

[57] ABSTRACT

The invention involves the supercritical or near-critical fluid disruption of microbial cells and extraction of intracellular components. First, a solvent that is a gas at ambient conditions and that has a critical temperature of between 0° and 100° C. is selected. This solvent is brought to near-critical pressure or higher and to near-critical temperature. The solvent then is combined with a slurry of cells to saturate the cells with the solvent under the prescribed conditions. Next, the pressure is released to cause a pressure drop which results in partial disruption of the cell membrane and release of solvent and other materials from the cell. Novel apparatus and associated methods are provided for carrying out the foregoing process continuously.

10 Claims, 16 Drawing Sheets

EFFECT OF SUPERCRITICAL FLUID ON THE MICROBIAL CELL DISRUPTION OF
BACILLUS SUBTILIS (93 g DCW/l)

| EXP.# | SCF | TEMP. (C) | PRESS. (psig) | R.T. (min) | DEL CPRO (%) | DEL CNUCL (%) |
|---|---|---|---|---|---|---|
| MCD-82 | N2O | 41 | 4,900 | 122 | 41.3 | 70.7 |
| MCD-90 | CO2 | 40 | 4,900 | 120 | 22.7 | 6.6 |
| MCD-88 | N2 | 41 | 5,100 | 120 | 0.0 | 20.2 |

FIG. 6

EFFECT OF SUPERCRITICAL FLUID ON THE MICROBIAL CELL DISRUPTION OF
SACCHAROMYCES CEREVISIAE (69 g DCW/l)

| EXP.# | SCF | TEMP. (C) | PRESS. (psig) | R.T. (min) | DEL CPRO (%) | DEL CNUCL (%) |
|---|---|---|---|---|---|---|
| MCD-33 | N2O | 40 | 4,800 | 25 | 26.6 | 67.0 |
| MCD-54 | N2O | 40 | 4,500 | 15 | 17.1 | 82.6 |
| MCD-58 | CO2 | 40 | 4,700 | 26 | 29.6 | 77.5 |
| MCD-76 | N2 | 40 | 4,500 | 25 | 5.5 | 20.5 |

FIG. 7

EFFECT OF TEMPERATURE ON THE MICROBIAL CELL DISRUPTION OF
ESCHERICHIA COLI (39 g DCW/l) BY NITROUS OXIDE

| EXP.# | TEMPERATURE (C) | PRESSURE (psig) | R.T. (MIN) | DEL CPRO (%) | DEL CNUCL (%) |
|---|---|---|---|---|---|
| MCD-99 | 29 | 4,800 | 25 | 0.0 | 6.5 |
| MCD-96 | 41 | 4,900 | 25 | 0.0 | 24.4 |
| MCD-100 | 30 | 4,800 | 120 | 8.9 | 16.6 |
| MCD-101 | 41 | 5,000 | 120 | 11.8 | 46.3 |

*FIG. 15*

EFFECT OF TEMPERATURE ON THE MICROBIAL CELL DISRUPTION OF
BACILLUS SUBTILIS (62 g DCW/l) BY NITROUS OXIDE

| EXP.# | TEMPERATURE (C) | PRESSURE (psig) | R.T. (MIN) | DEL CPRO (%) | DEL CNUCL (%) |
|---|---|---|---|---|---|
| MCD-77 | 29 | 4,700 | 60 | 0.3 | 10.6 |
| MCD-78 | 40 | 4,800 | 60 | 20.7 | 26.5 |

*FIG. 16*

EFFECT OF TEMPERATURE ON THE MICROBIAL CELL DISRUPTION OF
SACCHAROMYCES CEREVISIAE (68 g DCW/l) BY CARBON DIOXIDE

| EXP.# | TEMPERATURE (C) | PRESSURE (psig) | R.T. (MIN) | DEL CPRO (%) | DEL CNUCL (%) |
|---|---|---|---|---|---|
| MCD-71 | 21 | 2,400 | 16 | 21.13 | 17.47 |
| MCD-72 | 23 | 4,300 | 30 | 24.82 | 20.60 |
| MCD-73 | 33 | 1,100 | 24 | 17.54 | 38.74 |
| MCD-74 | 32 | 2,400 | 25 | 17.29 | 38.30 |
| MCD-75 | 32 | 4,300 | 26 | 7.03 | 55.25 |
| MCD-56 | 40 | 1,450 | 26 | 28.13 | 73.61 |
| MCD-57 | 40 | 3,100 | 25 | 28.11 | 79.17 |
| MCD-58 | 40 | 4,700 | 26 | 24.57 | 77.48 |

FIG. 18

EFFECT OF TEMPERATURE ON THE MICROBIAL CELL DISRUPTION OF
SACCHAROMYCES CEREVISIAE (68 g DCW/l) BY ETHYLENE

| EXP.# | TEMPERATURE (C) | PRESSURE (psig) | R.T. (MIN) | DEL CPRO (%) | DEL CNUCL (%) |
|---|---|---|---|---|---|
| MCD-102 | 6 | 1,650 | 120 | 0.0 | 4.2 |
| MCD-103 | 22 | 1,650 | 132 | 18.64 | 52.7 |

FIG. 19

SUPERCRITICAL FLUID DISRUPTION OF AND EXTRACTION FROM MICROBIAL CELLS

This application is a continuation, of application Ser. No. 07/799,767, filed Nov. 27, 1991, now abandoned which is a continuation of Ser. No. 07/680,610, filed Apr. 1, 1991, now abandoned which is a continuation of Ser. No. 07/382,858, filed Jul. 20, 1989 now abandoned.

This invention relates in general to the downstream purification of cellular products and more particularly to methods and apparatuses for the extraction of products from microbial cells using supercritical fluids and explosive decompression.

BACKGROUND OF THE INVENTION

Genetically engineered proteins have been gaining increased importance as potential therapeutics for human and animal health care, as well as industrial applications. Currently, such proteins are produced by several similar series of processing steps which can be generically summarized as follows: (1) Protein production by cell culture; (2) Cell breakage, extraction and removal; (3) Primary purification or initial fractionation; (4) High resolution chromatographic purification; and (5) Formulation and encapsulation. Downstream purification (steps 2–5) typically accounts for a large percent of the total production costs.

As cells are relatively expensive raw materials, high product and activity yields are of prime importance. For large scale operations, the preferred methods of cell disruption are high-pressure homogenization and wet milling in high-speed agitator bead mills. These techniques employ high shear forces and generate heat, both factors which are potentially damaging to the protein being recovered.

Furthermore, conventional industrial-scale microbial cell disruption techniques are non-selective in that the cell wall is attacked at multiple locations leading to the formation of small cell wall fragments. This increases the downstream purification burden because such fragments are difficult to separate from the process stream and may lead to the fouling of adsorbents and the clogging of chromatographic columns (steps 3 and 4 above). While such cell disruption is not usually a requirement in the recovery of intracellular proteins, in most conventional processes, cell wall fragmentation is a consequence.

It is an object of the invention to provide a method and an apparatus for extracting material from cells, which method avoids the above-mentioned drawbacks.

Another object of the invention is to provide a method for microbial cell disruption that reduces cell wall fragmentation.

Still another object of the invention is to provide a method of cell disruption which only minimally exposes the cells to high shear forces and little or no heat generation.

Yet another object of the invention is to provide an improved method of microbial cell disruption that simplifies the purification scheme, reduces processing time and favorably impacts production costs.

These and other objects are achieved by the methods and apparatus of the invention.

SUMMARY OF THE INVENTION

The invention combines the beneficial aspects of explosive decompression and supercritical fluid extraction. First, a solvent that is a gas at ambient conditions and that has a critical temperature between 0° and 100° C. is selected. Preferably, the critical temperature is between 0° and 50° C. This solvent is brought to near-critical pressure or higher and to near-critical temperature. The solvent then is combined with a slurry of intact cells to saturate the cells with the solvent under the prescribed conditions. Next, the pressure is released, preferably suddenly, to cause a pressure drop which results in partial disruption of the cell membrane and release of solvent and other materials from the cell. Surprisingly, the cell walls are less fragmented than when using conventional microbial cell disruption techniques, and yet the yield of proteins and nucleic acids from the cells is greatly improved. Further, the cells are exposed to minimal shear forces and there is no heat generation which would adversely affect yield.

According to one aspect of the invention, conditions are applied to allow preferential collection of proteins or nucleic acids. First, the mixture of solvent and cells is maintained at just below the critical temperature of the solvent while subjecting the mixture to pressures at or above the critical pressure of the solvent. When the pressure is released, proteins are selectively expressed from the cell, with little or no nucleic acids expressed. After removing the solvent containing the expressed protein, new solvent optionally may be added and the mixture then may be repressurized and maintained at a temperature above the solvent's critical temperature. Explosive decompression under these conditions results in nucleic acids being released from the cells, along with additional proteins.

Preferably, the solvent when combined with the cells result in a mixture having a pH that is close to the pH at which the cells are normally cultured. For example, when working with prokaryotes cultured at neutral pH, the preferred solvent is neutral and only slightly polar such as nitrous oxide ($N_2O$).

According to another aspect of the invention, microbial cell disruption and extraction of intracellular components are carried out continuously in a novel apparatus. A slurry of cells is continuously introduced into a high-pressure soaking vessel. Likewise, a solvent at near-critical temperature also is continuously introduced into the vessel. The solvent and cells are maintained at or near critical temperature and are continuously mixed. All the while, a portion of the solvent and cells is continuously removed from the vessel and is depressurized. The broth containing the expressed cellular material is then continuously collected.

Preferably the vessel has an upstream end and a downstream end, with the slurry of cells and the solvent being introduced under pressure into the upstream end. The solvent and cells are caused to move continuously from the upstream end toward the downstream end of the vessel while continuously mixing the solvent and cells in the vessel. The solvent and cells are then removed continuously from the downstream end of the vessel and depressurized.

The vessel may include means for maintaining at a preset temperature the solvent and cells in the vessel. The vessel also may include means for mixing the solvent and cells within the vessel. The mixing means may be a blade or other mechanically actuated mixer or may be a conduit constructed and arranged to withdraw and recirculate a portion of the contents of the vessel. The vessel also may include recirculation means independent of the mixing means for recirculating solvent, cells or both back to the upstream end of the vessel.

These and other features of the invention are described in greater detail below.

BRIEF DESCRIPTION OF THE DRAWINGS

FIG. 6 is a table showing the recovery of nucleic acids and of protein from Bacillus subtilis using $N_2O$, $CO_2$ and $N_2$;

FIG. 7 is a table showing the recovery of nucleic acids and of proteins from Saccharomyces cerevisiae using $N_2O$, $CO_2$ and $N_2$;

FIG. 15 is a table showing the effect of temperature on the microbial cell disruption of E. coli;

FIG. 16 is a table showing the effect of temperature on the microbial cell disruption of Bacillus subtilis;

FIG. 18 is a table showing the effect of temperature on the microbial cell disruption of Saccharomyces cerevisiae using $CO_2$;

FIG. 19 is a table showing the effect of temperature on the microbial cell disruption of Saccharomyces cerevisiae using ethylene.

DETAILED DESCRIPTION OF THE PREFERRED EMBODIMENT

Figure 1:
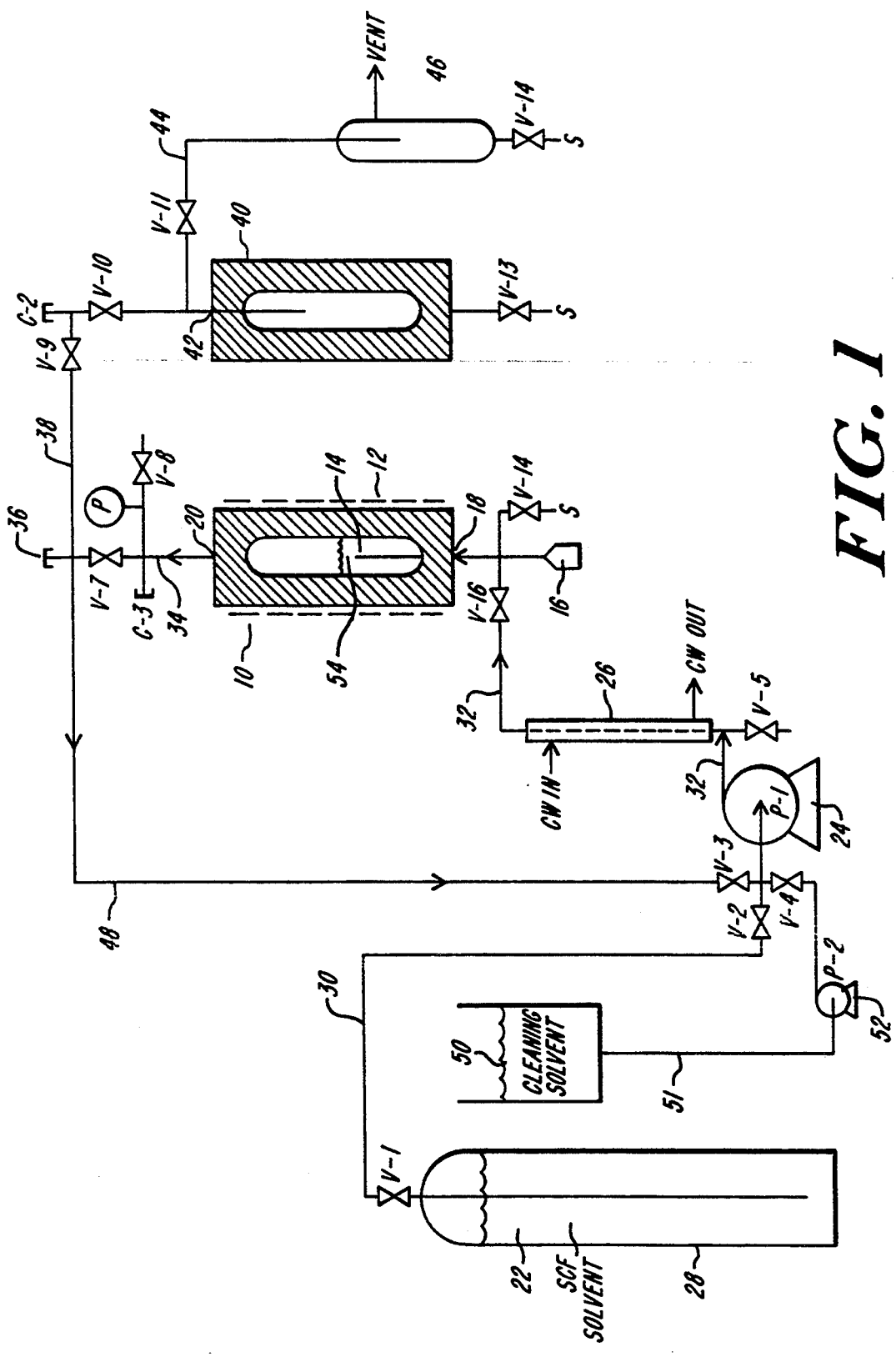
FIG. 1 is a schematic illustration of one apparatus of the invention.

An apparatus of the invention is depicted in FIG. 1. It includes a soaking chamber 10 in which a slurry of cells and solvent are mixed for a specified time under controlled conditions. The particular soaking chamber 10 employed was a high-pressure vessel having a capacity of 60 cc and an operating pressure rating of 5,000 psig at 25° C. (Model No. M1-TU4, Penberthy-Houdaille, Inc., Prophetstown, Ill.). The soaking chamber 10 is heat-traced with heating tape 12, which heating tape 12 in turn is connected to a thermocouple 14 inserted into the center of the soaking chamber 10. The heating tape 12 and the thermocouple 14 are connected to a proportional controller 16 (Model No. CN-3000 Omega, Inc., Stamford, Conn.) such that the temperature within the soaking chamber 10 may be preset and maintained automatically.

The soaking chamber 10 has a bottom port 18 and a top port 20. The bottom port 18 communicates via various conduits with a source of solvent 22. Between the source of solvent 22 and the bottom port 18 of the soaking chamber 10 is a high-pressure compressor 24 for introducing solvent 22 into the soaking chamber 10 as well as for compressing solvent 22 in soaking chamber 10 up to a prespecified operating pressure. The particular compressor employed was a single-ended diaphragm compressor which can compress gas or liquid up to 10,000 psi at a flow rate of 40 standard liters per minute (Model No. J-46-13411, Superpressure Gas Compressor, Newport Scientific, Jessup, Md.).

Between the compressor 24 and the bottom port 18 of the soaking chamber 10 is a heat exchanger 26 used to remove the heat of compression generated from the compression of solvent 22. The heat exchanger employed was a circulating, refrigerated water-bath capable of cooling the discharge line of the compressor to as low as 5° C. (Model No. HX-150, NESLAB, Inc., Concord, N.H., 15,300 Btu/hr capacity).

Conduits transfer the solvent 22 from a solvent container 28 to the soaking chamber 10. Solvent 22 exits from the solvent container 28 through valve V-1 and is delivered into the compressor 24 via solvent conduit 30 and valve V-2. Compressed solvent 22 exits the compressor 24 and is delivered via compressor discharge conduit 32 into the soaking chamber 10, passing on the way through heat exchanger 26, valve V-6 and bottom port 18.

The microbial slurry is introduced into the soaking chamber via the top port 20. The soaking chamber 10 is in fluid communication via top port 20 and slurry charge conduit 34 with a charge port 36 for introducing the slurry into the soaking chamber 10.

The soaking chamber 10 also is in fluid communication via the top port 20, slurry charge conduit 34 and blow-down conduit 38 with a blow-down chamber 40 into which the microbial slurry is sprayed upon release of the pressure in the soaking chamber 10. The blow-down chamber 40 employed also was a high-pressure vessel manufactured by Penberthy-Houdaille, supra (Model No. 1-TU7; 88 cc capacity). Upon release of the pressure, the cells may pass via slurry charge conduit 34 through valve V-7 and then via blow-down conduit 38 through valves V-9 and V-10 into blow-down chamber 40 via blow-down chamber top port 42.

Branching from blow-down conduit 38 between blow-down chamber top port 42 and valve V-10 is an overflow conduit 44. Overflow conduit 44 communicates via valve V-11 with low-pressure vessel 46 which vessel 46 acts to trap any spray carried over from the blow-down chamber 40.

Soaking chamber 10 also is provided with a recycle conduit 48. This recycle conduit 48 fluidly connects soaking chamber top port 20 and bottom port 18. Fluid may pass from the soaking chamber 10 via soaking chamber top port 20 into charge conduit 34. Charge conduit 34 in turn connects to recycle conduit 48 which is in fluid communication via valve V-3 with solvent conduit 30 between valve V-2 and compressor 24. Solvent conduit 30 communicates with compressor 24 which in turn communicates via compressor discharge conduit 32 with bottom port 18.

A cleaning fluid 50 also communicates with soaking chamber 10, making its connection between valve V-2 and compressor 24. Cleaning fluid pump 52 pumps cleaning fluid 50 through compressor 24 and conduit 32 via valve V-4 and into soaking chamber 10, blow-down chamber 40, low pressure trap 46 and connecting conduits.

The device shown in FIG. 1 and described above may be operated as follows: As an initial condition, all valves are in the fully closed position. A microbial slurry first is introduced through charge port 36 into the soaking chamber 10 when conduit valves V-7, V-10 and V-11 are fully opened, all other valves being closed. Valves V-1 and V-3 then are fully opened and valves V-2 and V-9 are slightly opened, allowing solvent to displace the air in solvent conduit 30, soaking chamber 10, recycle conduit 48 and blow-down conduit 38. Valve V-9 then is fully closed and the soaking chamber 10 is slowly pressurized to the pressure within the solvent container 28 by incrementally opening valve V-2. Pressurization is gradual to minimize thermal transients which result from the heat of compression. After stabilization of pressure and temperature, the valve V-2 is closed, valve V-6 is opened and compressor 24 is activated to circulate solvent 22 through the microbial slurry 54 in soaking chamber 10. The soaking chamber 10 then may be charged to near-critical or supercritical pressure as desired. With valve V-7 still open from the preceding steps, the system is dead-headed by closing valve V-3, and then charged to desired pressure by opening valve V-2 to feed more solvent 22 through the compressor 24. V-2 is then closed and V-3 opened for further circulation of the supercritical fluid. After The solvent 22 has circulated through the microbial slurry 54 to an extent sufficient to saturate the cells with solvent 22, the compressor 24 is turned off, valve V-6 is closed and valve V-9 is opened as rapidly as possible to allow the depressurization of soaking chamber 10 to atmospheric pressure. (Valves V-10 and V-11 are opened at this stage. Atmospheric pressure is reached because of an open vent in the low pressure vessel.) Disrupted cells and broth may then be collected from the soaking chamber 10 via valve V-12, from the blow-down chamber 40 via valve V-13 and from the low pressure vessel 46 via valve V-14. The lines are then purged with compressed air, preferably at about 200 psig, to remove any entrapped materials which are collected. Next, valve V-6 is opened and the system is fully decompressed, followed by again purging the system with air and draining of soaking, blow-down and low pressure chambers.

The apparatus of FIG. 1 may be cleaned by utilizing centrifugal cleaning pump 52 to circulate cleaning fluids such as 10% Clorox through the various conduits and vessels. The Clorox may be flushed out of the system using water pumped by the same cleaning pump 52.

Figure 2:
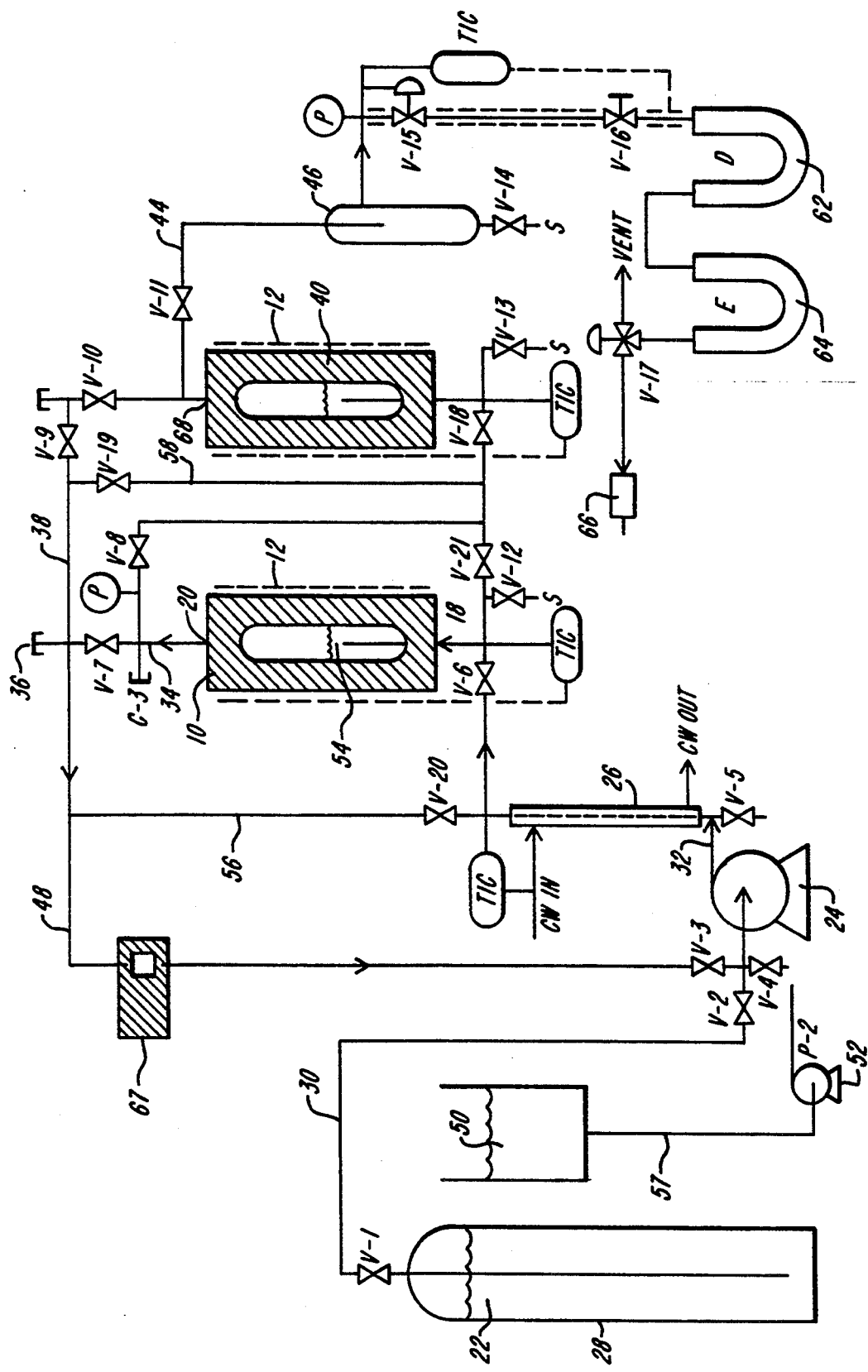
FIG. 2 is a schematic illustration of a modified version of the apparatus of FIG. 1.

The apparatus shown in FIG. 2 is a modification of that shown in FIG. 1, and includes certain features that are desirable for both research and industrial purposes. The soaking chamber 10 and the blow-down chamber 40 in this embodiment are high-pressure see-through vessels having an internal capacity of 100 cc and a maximum operating pressure of 10,000 psig at 25° C. (Model No. 28-T-51, Jerguson Gage & Valve Co., Burlington, Mass.). Alternatively, high pressure vessels such as Model No. OR0050SS11, Autoclave Engineers, Erie, Pa., can be utilized. These chambers 10, 40 are adapted to accommodate mechanical mixers, for example, magnetically coupled stirring devices.

Both soaking chamber 10 and blow-down chamber 40 are provided with pressure-equilibration conduits so that the chambers may be pressurized simultaneously from both ends. The pressure-equilibration conduit 56 for soaking chamber 10 fluidly connects recycle conduit 48 to compressor discharge conduit 32. Valve V-20 is located along the pressure-equlibration conduit 56 for controlling flow. The pressure-equilibration conduit 58 for blow-down chamber 40 fluidly connects blow-down conduit 38 to compressor discharge conduit 32, the connection located between soaking chamber 10 and blow-down chamber 40. Valve V-19 is located along the pressure-equilibration conduit 58 for controlling flow.

A second recycle conduit 60 provides for fluid communication between the slurry charge conduit 34 and the pressure-equilibration conduit 58, the connection to conduit 58 located between chambers 10 and 40. A flow valve V-8 is located on second recycle conduit 60. Another flow valve V-21 is located on the compressor discharge conduit 32 after valve V-12 and before the connection point of the second recycle conduit 60.

Unlike the apparatus of Fig. 1, the low-pressure vessel 46 of FIG. 2 does not vent directly to atmosphere. Rather, it fluidly connects via a back-pressure regulator valve V-15 and a flow rate metering valve V-16 to traps 62, 64. The back pressure regulator valve V-15 will be used to set the system pressure as well as to control depressurization. The flow metering valve V-16 will be used adjust the flow of material exiting the low-pressure vessel 46 into traps 62, 64. Valves V-15, V-16 are heated to avoid freeze-up due to solvent expansion upon depressurization.

The traps 62, 64 capture solutes which precipitate out of the solvent upon depressurization. Currently, glass wool in U-tubes are employed, although it will be recognized by one of ordinary skill in the art that many different types of traps may be used. The material exiting the traps 62, 64 is directed into a three-way valve V-17 which may be vented to atmosphere or may be directed to a flow meter 66 (e.g. a soap bubble flow meter or a standard gas meter).

The device shown in FIG. 2 may be operated in the same manner as described above in connection with FIG. 1. In this instance, the soaking chamber 10 would act as a mixing chamber, the blow-down chamber 40 would act to receive the depressurized contents of the soaking chamber 10 and the low-pressure vessel 46 would act as an overflow for blow-down chamber 40.

The device shown in of FIG. 2 also may be used to separate solvent from the microbial slurry to facilitate collection of materials from the solvent alone. In this instance, the soaking chamber 10 is brought up to the desired temperature and pressure and solvent is introduced through the compressor 24 substantially as described above in connection with the apparatus of FIG. 1. Then, with valves V-21, V-8, V-9 and V-19 closed, the compressor 24 is allowed to recirculate solvent through the soaking chamber 10. At the end of a specified recirculation-induced mixing Time, soaking chamber 10 is isolated and the solvent is routed to blow-down chamber 40 which now acts instead as an extraction chamber. In this instance, valves V-7, V-11, V-19 and V-20 are closed. Blow-down chamber 40 may be precharged with appropriate back extraction aqueous buffers of different pHs and ionic strengths with/without polar cosolvents such as methanol, acetone, ethylene glycol and such mixtures thereof for extracting material from the solvent 22. The solvent 22 then may be recirculated through this back extraction solvent in the blow-down chamber 40. In doing so, solvent exits the top port 68 of blow-down chamber 40, passes through blow-down conduit 38 and recycle conduit 48 and then is pumped back to the bottom port of blow-down chamber 40 by compressor 24. Recycle conduit 48 is preferably provided with a high pressure UV/VIS detector 67 which indicates the level of equilibration between the supercritical fluid solvent and the back extraction solvent in blow-down chamber 40.

The solute-depleted solvent may then be discharged from the system via low-pressure vessel 46 and traps 62, 64 by opening valve V-11, and regulating back-pressure valve V-15 and metering valve V-16. The back extraction buffer may then be recovered from blow-down chamber 40.

Traps 62, 64 may be rinsed with appropriate solvents and then cleaned, dried and returned to service. Thereafter, soaking chamber 10 will be depressurized by first opening valve V-11, and then rapidly opening V-7. The disrupted microbial slurry then will be collected from the various chambers as described above in connection with FIG. 1.

The solvent may be circulated through the soaking chamber 10 and the blow-down chamber 40 prior to isolating the slurry and solvent extraction. After such circulation, soaking chamber 10 may be isolated, and the above-described depressurization and sample recovery procedures repeated. This alternate method will allow investigation into whether or not the solvation of lipids and hydrophobic compounds in the solvent is capacity and/or time sensitive.

The apparatus in FIG. 2 also has the flexibility to handle solvents which are more dense than the microbial slurry. In this instance, the flow directions may be reversed so that the blow-down chamber 40 acts as the soaking chamber and the soaking chamber 10 acts as the blow-down chamber.

Figure 3:
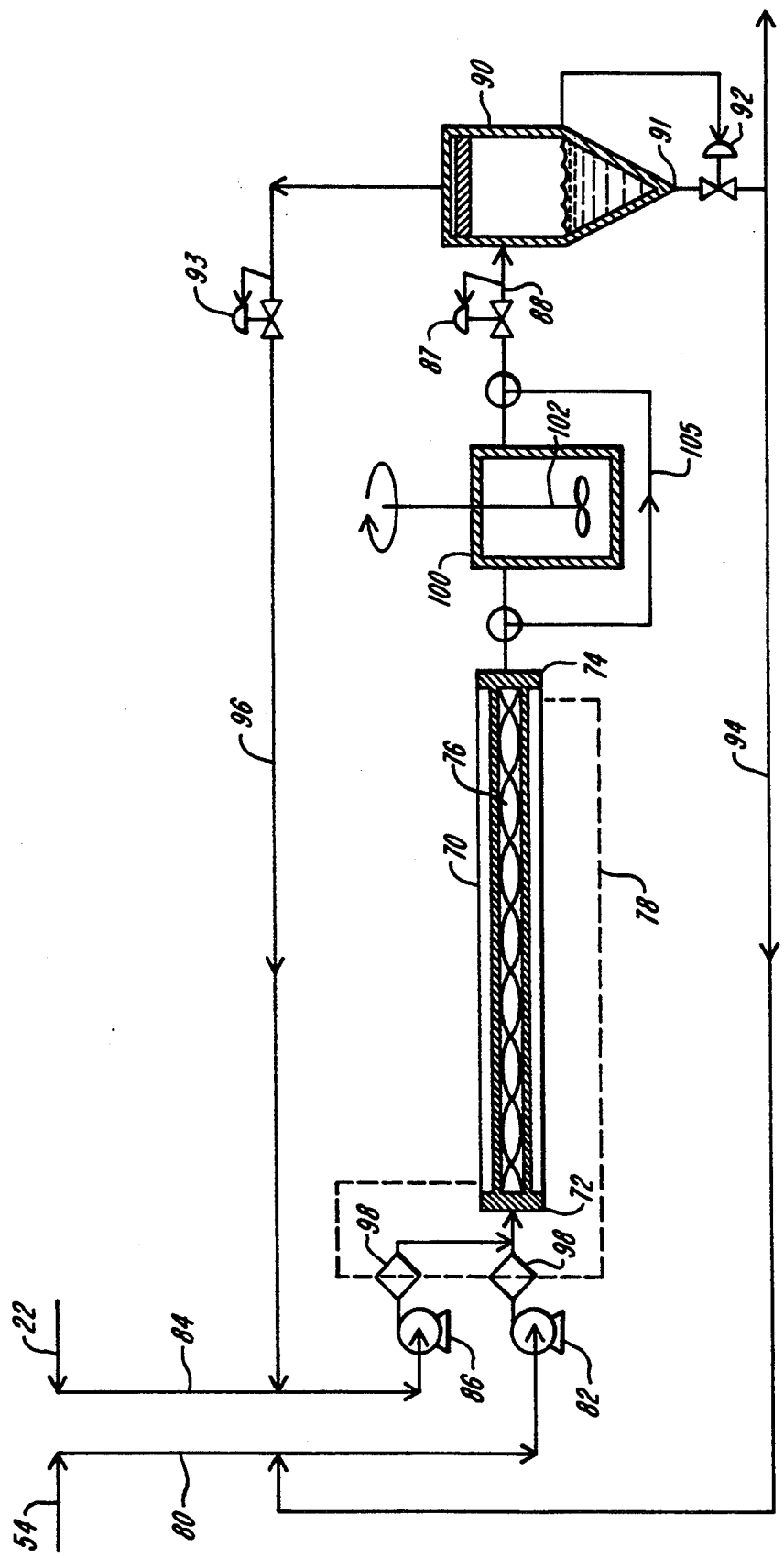
FIG. 3 is a schematic illustration of a preferred apparatus of the invention capable of continuous microbial cell disruption.

An embodiment of the apparatus of the invention intended for industrial use is shown in FIG. 3. The apparatus of FIG. 3 is designed for continuous operation. The apparatus includes a mixing chamber 70 in the form of an elongated cylinder having an inlet end 72 and outlet end 74. Disposed centrally throughout the mixing chamber 70 is a static mixer 76. The static mixer 76 mixes the microbial slurry 54 and the solvent 22 as the mixture is directed continuously from the inlet end 72 to the outlet end 74 of the mixing chamber 70. The mixing chamber 70 is jacketed and interfaced with a temperature control loop 78 which recovers the heat of compression of the solvent as well as any heat transferred from fermenters and centrifuges. The temperature control loop 78, of course, is capable of maintaining the contents of the mixing chamber 70 at a preset temperature.

A slurry conduit 80 for introducing a slurry of cells into the mixing chamber 70 communicates with the inlet end 72. A high-pressure slurry pump 82 is connected to the slurry conduit 80 for pumping the slurry of cells under pressure into the mixing chamber 70. A solvent conduit 84 is in fluid communication with the slurry conduit 80 downstream of the slurry pump 82. A compressor 86 is provided along the solvent conduit 84 for raising the pressure of the solvent 22 and of the mixture within the mixing chamber 70 to critical pressures and above. A discharge conduit 88 leads from the outlet end 74 of the mixing chamber 70 to a blow-down chamber 90. A back pressure regulator or valve 87 is placed along the discharge conduit 88 between the mixing chamber 70 and the blow-down chamber 90 for continuously releasing the pressure on the slurry of cells exiting from the mixing chamber 70.

The blow-down chamber 90 is constructed and arranged to allow effective gravity separation of the solvent and the disrupted microbial slurry. In the embodiment shown, the lower end of the blow-down chamber 90 is funnel-shaped for collecting the disrupted cells. At the bottom of The funnel is an exit port 91. A liquid level control valve 92 is attached at the bottom exit port of the blow-down chamber 90 for controlling the liquid level within the blow-down chamber. Material may be collected at this port 91 or recycled via slurry recycle conduit 94 to the slurry conduit 80 upstream of the slurry pump 82.

A solvent recycle conduit 96 fluidly connects the upper exit of the blow-down chamber 90 to the solvent conduit 84, upstream of the compressor 86. Another back-pressure regulator 93 is located on the solvent recycle conduit 96 for controlling the pressure within the blow-down chamber 90.

Heat exchangers 98 are located just downstream of the solvent compressor 86 and the slurry pump 82 to regulate the temperature of solvent leaving the compressor. The temperature control loop 78 also controls the heat exchangers 98.

In operation, a microbial cell slurry 54 may be fed directly from fermenters or centrifuges into the apparatus of FIG. 3. The slurry 54 is pumped with the high-pressure slurry pump 82 into the mixing chamber 70. Recycled solvent and any necessary make-up solvent are compressed and added to the microbial cell slurry downstream of the slurry pump 82 and upstream of the mixing chamber 70. The mixture of cells and solvent then is introduced continuously into the mixing chamber 70 and the mixture passes from the inlet end to the outlet end while being continuously mixed. The mixture continuously exits from the mixing chamber 70. As it exits, it is rapidly expanded through the heated, pressure-reduction valve 87 and is tangentially ejected into the blow-down chamber 90. Once in the blow-down chamber 90, the disrupted microbial slurry settles to the bottom and the solvent 22 stays on top. The separated solvent then may be recycled and used again. The disrupted slurry may be collected or may be recycled to increase the average residence time through the mixing chamber 70.

The pressure of the blow-down chamber may be maintained at pressures ranging from atmospheric to that of the mixing chamber. For a dominant coloration or permeability improvement mechanism, the pressure in the blow-down chamber 90 may be maintained at pressures relatively close to the operating pressures of the mixing chamber 70.

The continuous flow apparatus also may include a soaking chamber between the mixing chamber 70 and the blow-down chamber 90. Such a soaking chamber 100 will allow for a longer exposure time between the SCF solvent and the microbial cells; the soaking chamber may also accommodate mechanical mixers 102 to further facilitate the saturation of each microbial cell with SCF solvent. The soaking chamber can be by-passed by allowing the mixture of supercritical fluid and microbial slurry to flow directly from the mixing chamber 70 to blowdown chamber 90 via bypass loop 105.

Using the apparatus shown in FIG. 1 and described above, several organisms and several solvents were tested according to the invention. The organisms tested were: (1) *E. coli*, a Gram-negative bacterium; (2) *Bacillus subtilis*, a Gram-positive bacterium; and (3) *Saccharomyces Cerevesiae* (Baker's Yeast), a fungus.

*E. coli*. The *E. coli* was obtained from the *E. coli* genetic stock center, maintained by the Yale University School of Medicine (Culture No. 4401). Stock cultures of *E. coli* are maintained on agar slants at 420 C., and are transferred monthly.

The inoculum was prepared by streaking one loopful of cells from an agar slant onto an LB plate and grown up overnight. Individual colonies from this plate were used to inoculate 500 ml shake flasks containing 50 ml of medium. Shake flasks were grown up overnight at 37° C. on a rotary shaker operating at 200 rpm. After microscopic examination of the broth to ensure that no obvious contamination was present, the contents of the 500 ml shake flasks were transferred to 4,000 ml shake flasks containing 500 ml of medium. 4,000 ml shake flasks were similarly cultivated on the rotary shaker until cells reached mid-exponential phase (about 300 Klett units), whereupon the contents of one flask were used as inoculum for bench scale fermentation after again examining the culture microscopically.

Fermentations were started with 4.4% (v/v) inoculum in 11.5 liters of working volume. Fermentations were conducted at 16.7 psig, 37° C. and a pH of 7.0 in a 14 liter Chemap LF fermenter, and were run fed-batch with respect to glycerol. The pH of the material was controlled through the automatic addition of concentrated ammonium hydroxide when broth pH, as monitored by a sterilizable Ingold pH electrode, fell below pH 6.9. The aeration rate was maintained at 11 slpm (approximately 1 volume of gas per volume of liquid per minute). The agitation rate, initially 700 rpm, was gradually increased to 1,000 rpm during the course of fermentation so as to keep the partial pressure of oxygen in the bulk liquid phase 10% above air saturation values in order to avoid oxygen transfer limitations. The partial pressure of oxygen in the broth was monitored with the use of a galvanic oxygen electrode, and a Perkin-Elmer Mass Spectrometer was used for online analysis of inlet and exit gas compositions. Hourly samples were also taken for subsequent off-line analysis. Cell mass was determined using a Klett-Summerson Colorimeter calibrated to actual dry cell weight. Reversed phase HPLC employing a differential refractometer was used to determine broth composition.

Upon adequate biomass production, as inferred from cell mass measurements made on offline broth samples, the temperature set point of the fermenter was reduced to 20° C. Within 5 minutes of changing the temperature setpoint, the temperature of the broth fell to 21° C. and the metabolic activity of the culture (as seen by online gas data) was essentially suspended. The vessel contents where were harvested into a 20 liter Nalgene carboy. This carboy, fitted with an exhaust spigot at the base, was immediately placed at 4° C. After overnight gravity sedimentation of approximately 11 liters of biomass, the concentrated (sedimented) cell suspension—about 3 liters—at the bottom of the carboy was transferred through the exhaust spigot into large centrifuge tubes (each with a working volume of 250 ml) for centrifugation. Balanced samples were then centrifuged for 20 minutes at 5,000 rpm in a Sorvall 5B refrigerated centrifuge operating between 4° C. and 10° C. After decanting the supernatant, cell paste (occupying about 40 ml of the original 250 ml) was manually removed from the centrifuge tubes and stored at 4° C. The final concentration of the *E. coli* cell slurry was 275 grams dry cell weight per liter (g DCW/1).

*Saccharomyces Cerevisiae* Baker's yeast was aerobically grown in a fed-batch mode with glucose as the only limiting nutrient at a temperature of 30° C. and a pH of 5.0. Dissolved gas was kept above 15% through appropriate increase of air flow and agitation. Glucose was fed continuously; the glucose flow was determined by a computer control strategy which avoids ethanol production and keeps the specific growth rate around 0.22 1/hr. Ammonia was used as the nitrogen source and was fed as needed vis-a-vis a pH controller. The final cell density reached at the moment of harvesting was 51 grams dry cell weight per liter (g DCW/1).

The cells were harvested after cooling down the fermenter to 22° C., whereupon 3,200 ml of broth was collected for gravity sedimentation. After 48 hours, the supernatant was withdrawn and 1,200 ml of concentrated suspension was collected. The concentrated suspension contained approximately 136.0 g DCW/1 since gravity sedimentation concentrated the suspension by a factor of 2.67.

*Bacillus Subtilis*. Cultures of *B. subtilis* were obtained from the ATCC, Rockville, Md. (*Bacillus subtilis*, ATCC No. 21394). Stock cultures were maintained on Schaeffer sporulation agar (Schaeffer et al., 1965). To develop an inoculum, spores from a plate of Schaeffer sporulation agar were transferred to a plate of DIFCO nutrient agar in order for the spores to germinate into vegetative cells. A single colony was then transferred to a test tube containing 10 ml of the growth medium. After overnight growth, the 10 ml culture was used to inoculate a 900 ml culture growth medium. Growth was then continued until the 900 ml culture reached 200 Klett units, whereupon the culture was used to inoculate the main 12 liter fermenter. Microscopic observations were conducted at all stages of transfer to ensure that a pure culture was achieved.

Fermentation medium was designed to keep sporulation to a minimum. The fermentation was conducted at 34° C. and at a pH of 7.0. The pH of the material was controlled by the automatic addition of NaOH whenever the pH dropped below 6.85. The working volume, of approximately 11 liters, was supplied with air at a rate of one vvm (volume of air/volume of fermenter per minute) and continuously agitated at 500 rpm. After 13 hours of fermentation, the cell culture was harvested with a concentration of 4.8 g/l dry cell weight. At the time of harvest, the cells were estimated to have finished exponential growth and to be entering the stationary phase. No spores were detected by microscopic examination and cell lysis had not occurred to any significant extent.

After harvest, the culture was cooled to 4° C. and allowed to settle under gravity for three days. The concentrated cell suspension at the bottom of the carboy was then transferred to smaller containers. This post harvest concentration step yielded a dry cell weight concentration of 15 g DCW/1. The suspension was divided up into six aliquots (approximately 250 ml each) and centrifuged at 1,300 rpm for one hour at temperatures between 4° C. and 10° C. This centrifugation produced a light pellet which permitted most (95%) of the supernatant to be poured off easily before resuspending the pellet by vortexing. Upon combining all resuspended material, the final volume of the concentrated suspension was approximately 250 ml. To obtain more cell suspension, another 1,500 ml of dilute suspension was centrifuged at the same conditions for 30 minutes. Upon collection of the supernatant, the pelleted material from this centrifugation was resuspended and combined with the gravity sedimented and centrifuged cell slurry to give a final volume of concentrated cell suspension of approximately 300 ml. After mixing, duplicate 2.5 ml samples were taken for DCW analysis. The final concentration of the B. subtilis slurry was 93.3 g DCW/l.

Analytic Techniques. For E. coli and Baker's yeast, chilled samples of feed and product were centrifuged for 20 minutes at 3,000 rpm; the B. subtilis samples were centrifuged for 40 minutes at 3,000 rpm.

Total protein content of appropriately diluted samples of the supernatants was measured using a bicinchoninic acid (BCA) assay kit supplied by the Pierce Chemical Company, Rockford, Ill. In the BCA analysis, the protein molecule reduces cuprous ion in an alkaline medium to its cupric form which complexes the BCA into a purple reaction product which shows strong absorbance at 562 nm. Bovine serum albumin (BSA) was used as the protein standard using a 2 hour, room temperature incubation protocol. When measuring protein recovered from the disruption of E. coli cells, the BCA assay was relatively linear with concentration for a mixture of proteins.

UV absorbance of the suoernatant solutions were measured at 260 nm and 280 nm. Measured ratios of absorbance at 260 nm and 280 nm were approximately 2.0±10%. This ratio indicates that the absorptivity measurements primarily reflect the presence of nucleic acids since they have a peak absorbance at 260 nm which is approximately twice that at 280 nm. Proteins in the supernatant will also contribute to the absorptivity measurements since their peak absorbance is at 280 nm which is, at least for insulin, about 60% greater than their absorbance at 260 nm. Their contribution is, however, reduced because the specific absorbance of proteins is about 10 times less than the specific absorbance of nucleic acids, and may actually account for most of the ±10% in the ratio of absorbance at 260 and 280 nm. Absorbance at 260 nm and 280 nm thus were used as measures of the amount of nucleic acids present in the supernatants of the microbial cell slurries.

Enzymatic activities of alkaline phosphatase and glucose-6-phosphate dehydrogenase (G-6-PDH) were measured in selected supernatant samples. Alkaline phosphate was determined from the hydrolyric cleavage of p-nitrophenyl phosphate into p-nitrophenol which, in an alkaline medium, is converted to a yellow complex readily measured at 420 nm. Alkaline phosphatase assays were conducted with a kit purchased from the Sigma Chemical Co., St. Louis, Mo. G-6-PDH was measured by following the rate of formation of nicotinamide adenine dinucleotide hydrogen phosphate (NADPH) as an increase in UV absorbance at 340 nm. G-6-PDH reduces nicotinamide adenine dinucleotide phosphate (NADP) to NADPH in the presence of glucose-6-phosphate. G-6-PDH was measured using a Sigma Chemical kit.

Visible and ultraviolet absorbance measurements were made with a UV/VIS narrow bandwidth spectrophotometer (Model No. 100-10), manufactured by Hitachi, Tokyo, Japan.

All protein assays except one early assay involving E. coli (Example 4) were completed within hours (usually 2 to 4 but never more than 24) of test run completion since time studies suggested some aging effects after 48 hours for samples stored at 4° C. All nucleic acids and enzyme assays were conducted within 0.25 to 2 hours of test completion. All samples were stored at 4° C. before assays and before microscopic examination.

The solvents selected are gases at ambient conditions. For such solvents, when the critical pressure conditions are discontinued and ambient temperature and pressure suddenly resumed, a gaseous, high volume state is achieved. In addition, solvents were selected to have critical temperatures close to the optimal growth conditions of the cell cultures selected. This allowed the critical conditions to be achieved at a temperature nondestructive to the cells of their contents. Gaseous solvents such as $N_2$ with very low critical temperatures are not recommended because their supercritical or near critical densities at near ambient temperatures are not large enough to facilitate cell disruption and extraction by explosive disruption and permeability enhancement mechanisms.

The primary supercritical fluids tested were nitrous oxide ($N_2O$), carbon dooxide ($CO_2$) and nitrogen ($N_2$). Nitrous oxide was tested because of its polarity (0.2) and its critical temperature of 36.4° C., which is just about equal to the optimal growth temperatures of E. coli (37.0° C.), Baker's yeast (30.0° C.), and B. subtilis (34.0° C.). $CO_2$ was tested also because of its desirable critical temperature (31.0° C.) and further because of its low cost, nontoxicity, and nonflammability. Two tests were conducted with ethylene, primarily because of its low critical temperature of 9.2° C. The effectiveness of $N_2O$ and $CO_2$ was measured against $N_2$, the gas which is used in most conventional explosive decompression processes.

In the following examples, tests were conducted using the apparatus of FIG. 1 as described above. Unless otherwise stated, the concentration of E. coli was 69 g DCW/l; the concentration of B. subtilis was 93 g DCW/l; and the concentration of Baker's yeast was 68 g DCW/l.

EXAMPLE 1

Figure 4:
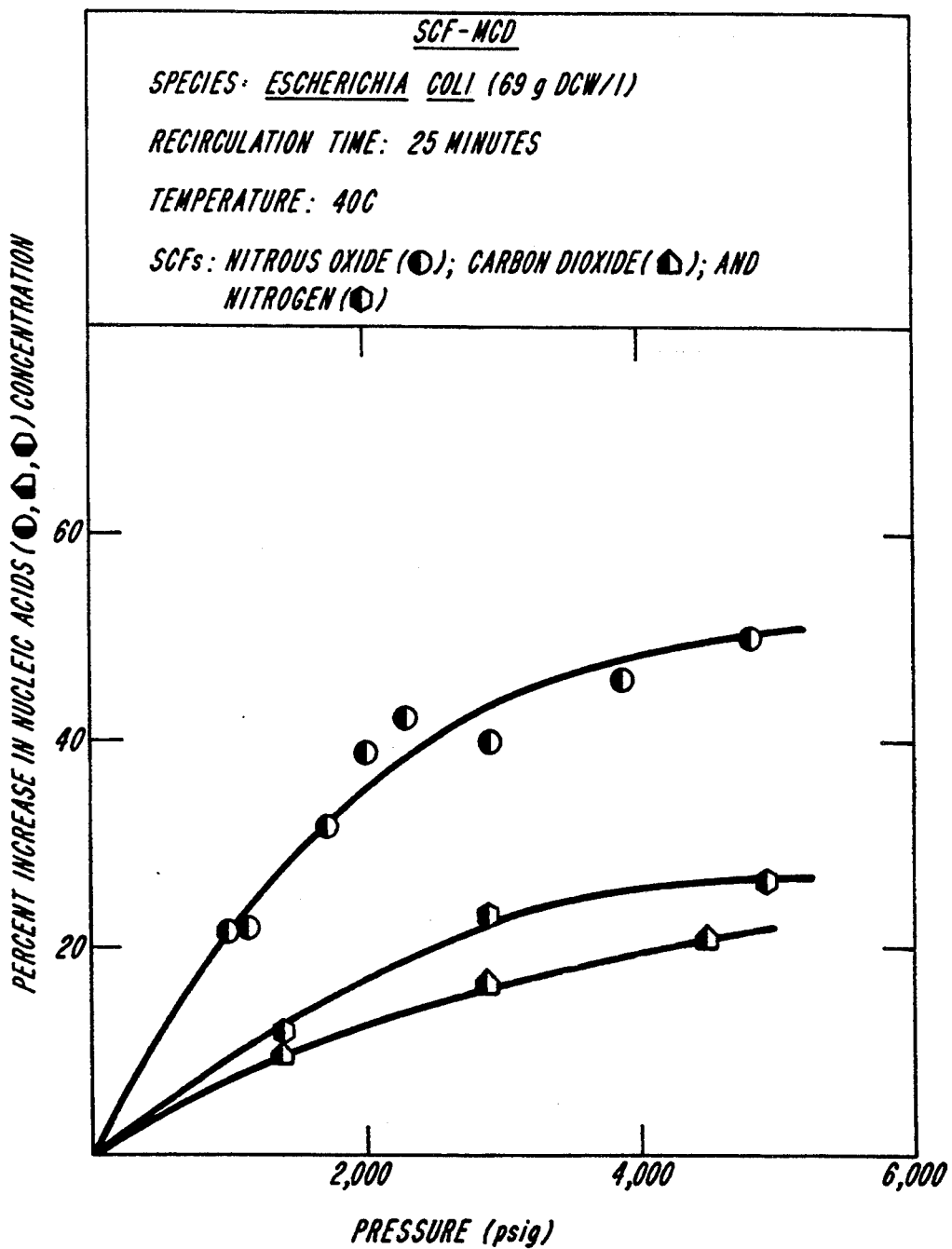
FIG. 4 is a graph illustrating the recovery of nucleic acids from E. coli using $N_2O$, $CO_2$ and $N_2$.
Figure 5:
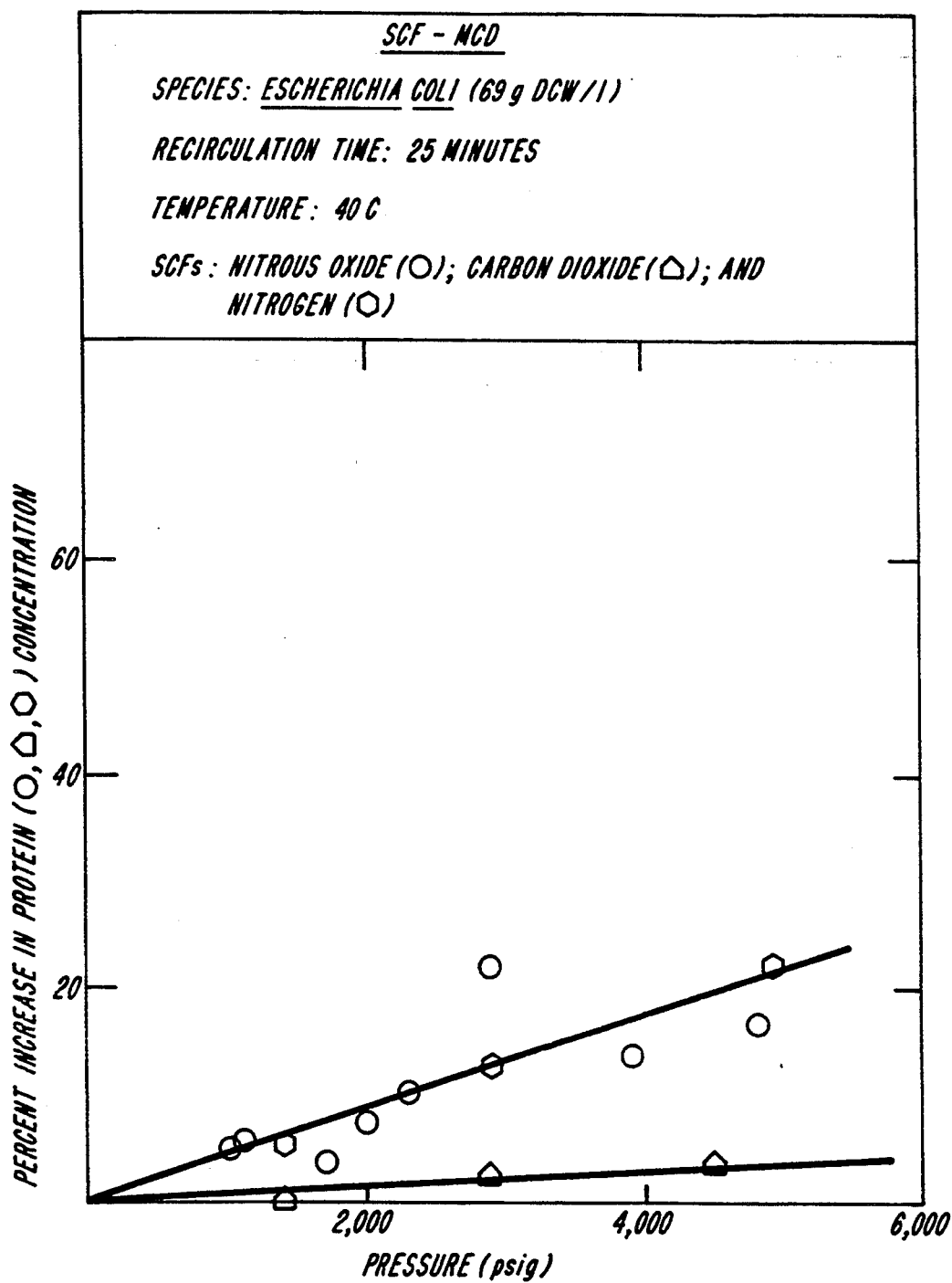
FIG. 5 is a graph illustrating the recovery of proteins from E. coli using $N_2O$, $CO_2$ and $N_2$.

The solvents $N_2O$, $CO_2$ and $N_2$ were tested for their efficacy in the supercritical microbial disruption of E. coli. Each test was conducted at a fixed temperature of 40° C. and a recirculation or exposure time of 25 minutes. Each solvent was tested at various pressures ranging from about 1400 psig to about 4900 psig. The recoveries of nucleic acids and of protein are respectively shown in FIGS. 4 and 5. $N_2O$ was the most effective solvent for recovering nucleic acids, being about twice as effective as either $CO_2$ or $N_2$. Using $N_2O$, the maximum recovery as a percentage of the total amount of nucleic acids present (yield) was about 50%. Using $N_2$, the yield was about 26%, and using $CO_2$, the yield was about 21%. For protein recovery, both $N_2O$ and $N_2$ were at least four times as effective as $CO_2$, with $N_2$ slightly better than $N_2O$.

Thus, for E. coli, $N_2O$ is the preferred solvent and $CO_2$ is relatively ineffective at the stated experimental conditions. $N_2O$ is a nonhomologous solvent for E. coli in that $N_2O$ is not involved in the biosynthetic pathway of E. coli.

EXAMPLE 2

The solvents $N_2O$, $CO_2$ and $N_2$ were tested for their efficacy in the supercritical microbial disruption of *B. subtilis*. Each test was conducted at a fixed temperature of 40° C. and a fixed pressure of about 5100 psig. Recirculation or exposure time was about 2 hours. The recovery of nucleic acids and protein is set forth in FIG. 6. $N_2O$ again was the most effective solvent for both nucleic acids and protein recovery. For nucleic acids recovery, $N_2O$ was about 11 times effective as $CO_2$ and about 3.5 times as effective as $N_2$. For protein recovery, $N_2O$ was about twice as effective as $CO_2$ and was infinitely more effective than $N_2$.

EXAMPLE 3

The solvents $N_2O$, $CO_2$ and $N_2$ were tested for their efficacy in the supercritical microbial disruption of *S. cerevisiae*. Each test was conducted at a fixed temperature of 40° C., a fixed pressure of about 4500 psig and a fixed recirculation time of about 25 minutes. The recovery of nucleic acids and protein is set forth in FIG. 7. $N_2O$ and $CO_2$ performed equivalently for nucleic acids and for protein recovery. Both of the solvents were more effective than $N_2$ (about 4 times as effective for recovery of both nucleic acids and protein).

EXAMPLE 4

Because $N_2O$ performed about as well or better than $CO_2$ and $N_2$ in the recovery of nucleic acids and protein from all organisms tested, $N_2O$ was used in tests regarding optimal pressure, temperature and recirculation times for the apparatus used (described herein as FIG. 1).

Figure 8:
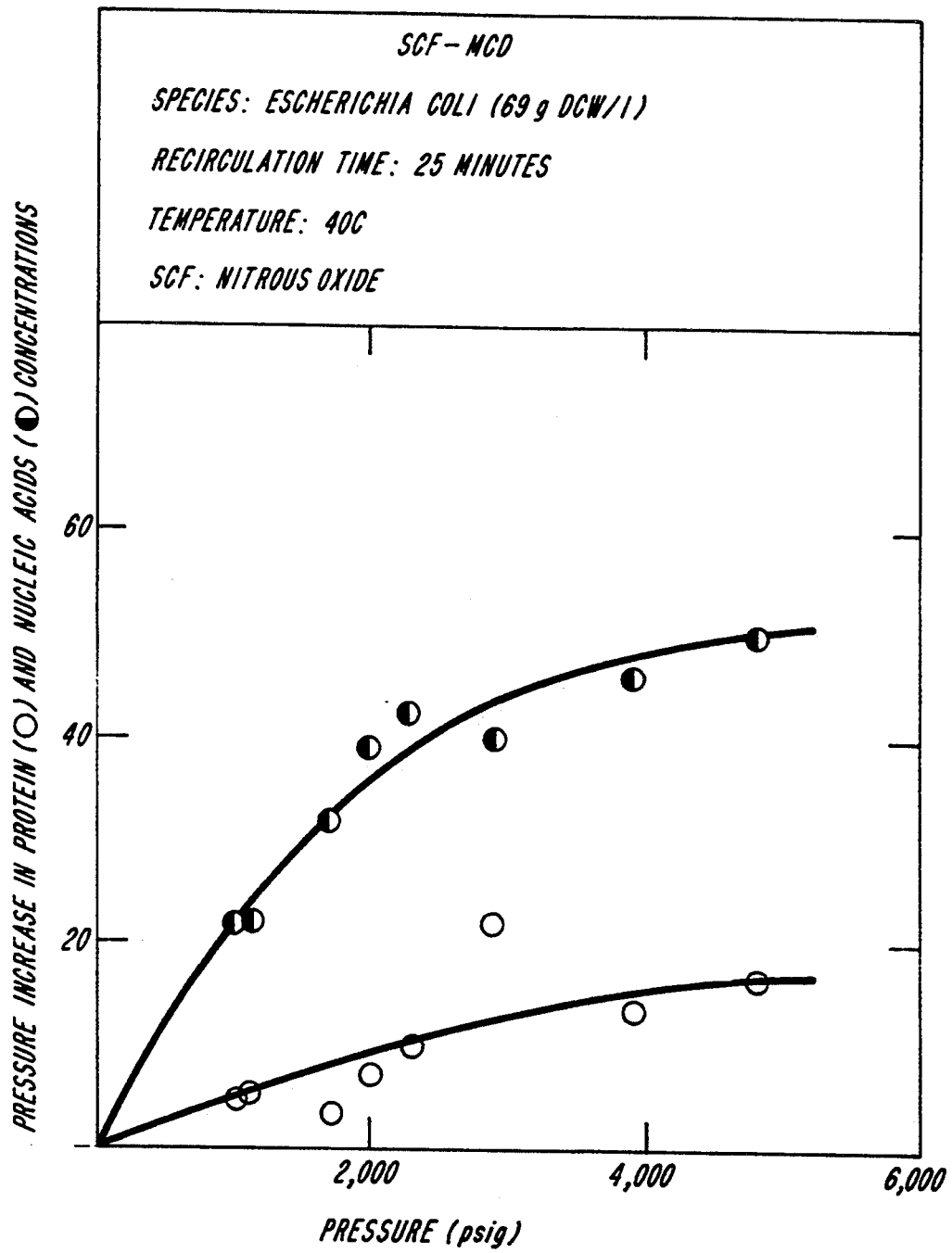
FIG. 8 is a graph illustrating the effect of pressure on the microbial cell disruption of E. coli.

The effect of pressure on the supercritical microbial disruption of *E. coli* using $N_2O$ was tested. The temperature and recirculation time were fixed at 40° C. and 25 minutes, respectively. Pressure was varied from about 1100 psig to 4800 psig. As pressure increased, the recovery of nucleic acids and protein also increased (FIG. 8). However, the relationship is a decaying one with a maximum recovery leveling off around 5000 psig.

Figure 9:
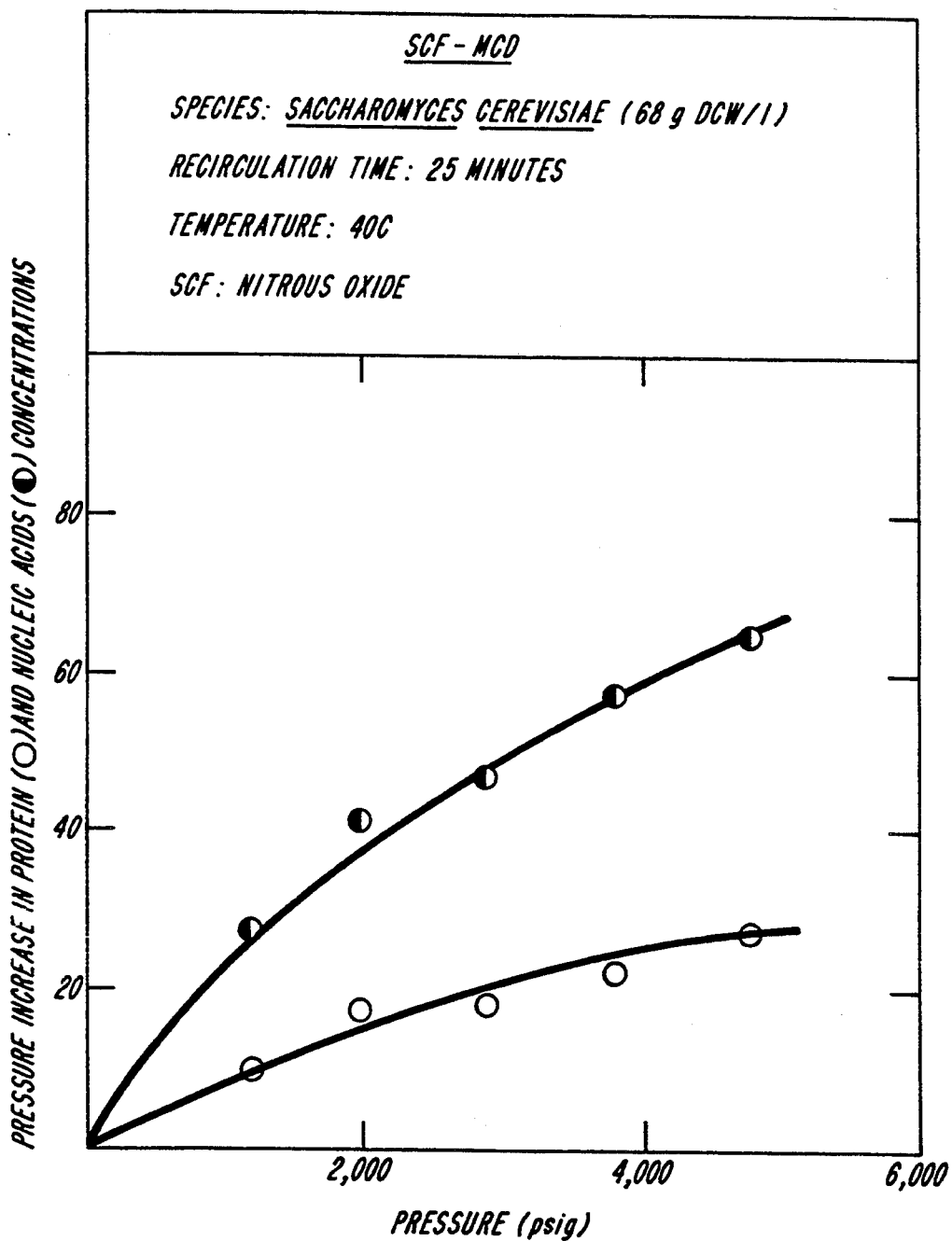
FIG. 9 is a graph illustrating the effect of pressure on microbial cell disruption of Saccharomyces cerevisiae.

The effect of pressure on the supercritical microbial disruption of Baker's yeast using $N_2O$ was also tested. The temperature and recirculation time were fixed at 40° C. and 25 minutes respectively. Pressure was varied from about 1100 psig to 4800 psig. As pressure increased, the recovery of nucleic acids and protein also increased (FIG. 9). However, the relationship was more linear than that for *E. coli*, indicating that higher pressures may result in even higher recovery efficiencies.

EXAMPLE 5

Figure 10:
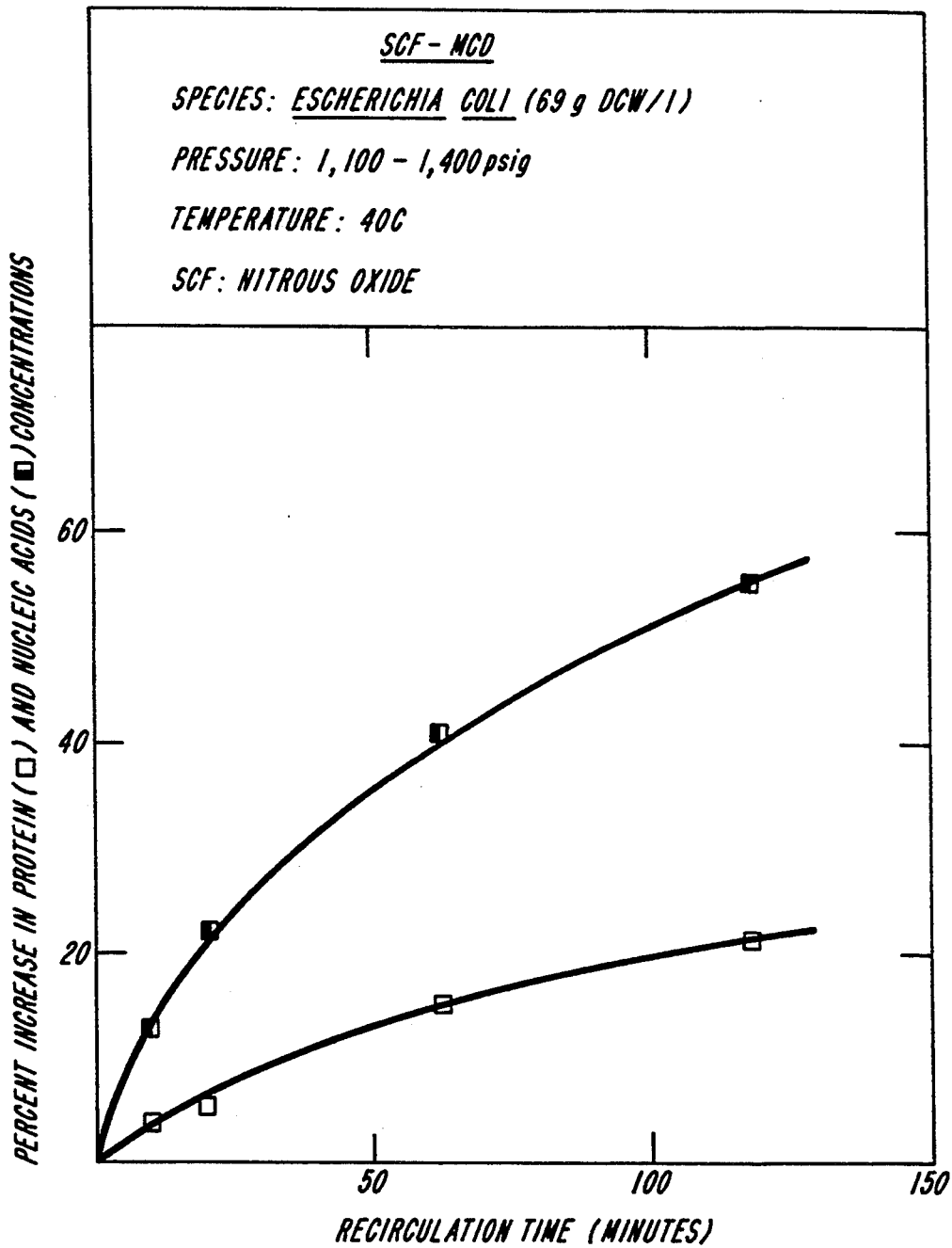
FIG. 10 is a graph illustrating the effect of exposure or recirculation time on the microbial cell disruption of E. coli.

The effect of recirculation or exposure time on the supercritical fluid microbial disruption of *E. coli* using $N_2O$ was tested. The temperature and pressure were fixed at 40° C. and 1200 psig respectively. Recirculation time was varied from 10 minutes to 118 minutes. The relationship between recirculation time and nucleic acids and protein recovery was positive and almost linear (FIG. 10). Nucleic acids recovery increased from 12.6% at 10 minutes recirculation to 55.6% at 118 minutes. Protein recovery increased from 3.5% at 10 minutes recirculation time to 21.1% at 118 minutes.

The recovery efficiencies at 1200 psig and 2 hours recirculation time are similar to those observed for *E. coli* using higher pressures (4800 psig) but lower recirculation times (25 minutes). This suggests that within certain constraints, longer recirculation times may be substituted for higher pressures and that yield is being controlled by mass diffusion of solvent into the cells.

EXAMPLE 6

Figure 11:
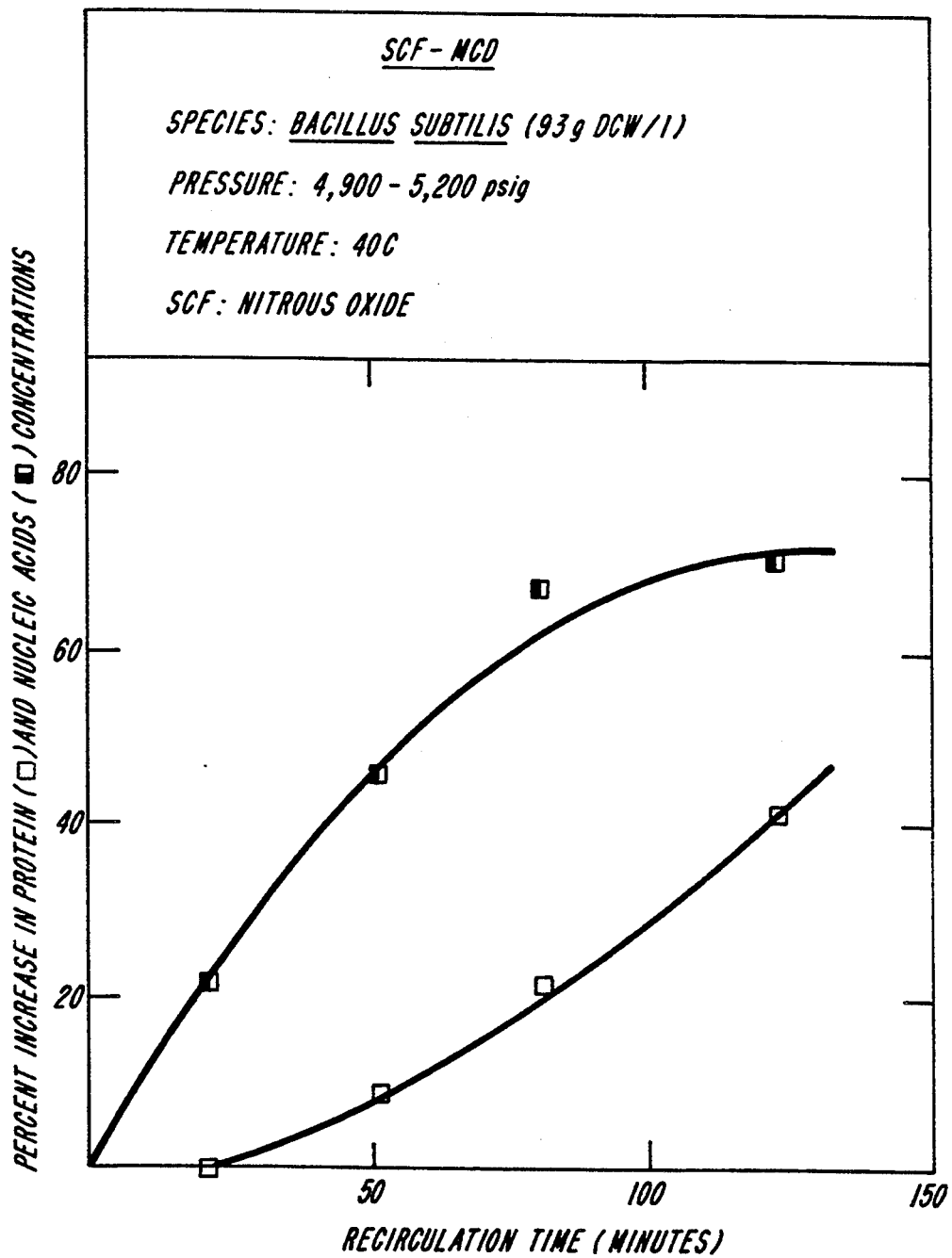
FIG. 11 is a graph illustrating the effect of exposure or recirculation time on the microbial cell disruption of Bacillus subtilis.
Figure 12:
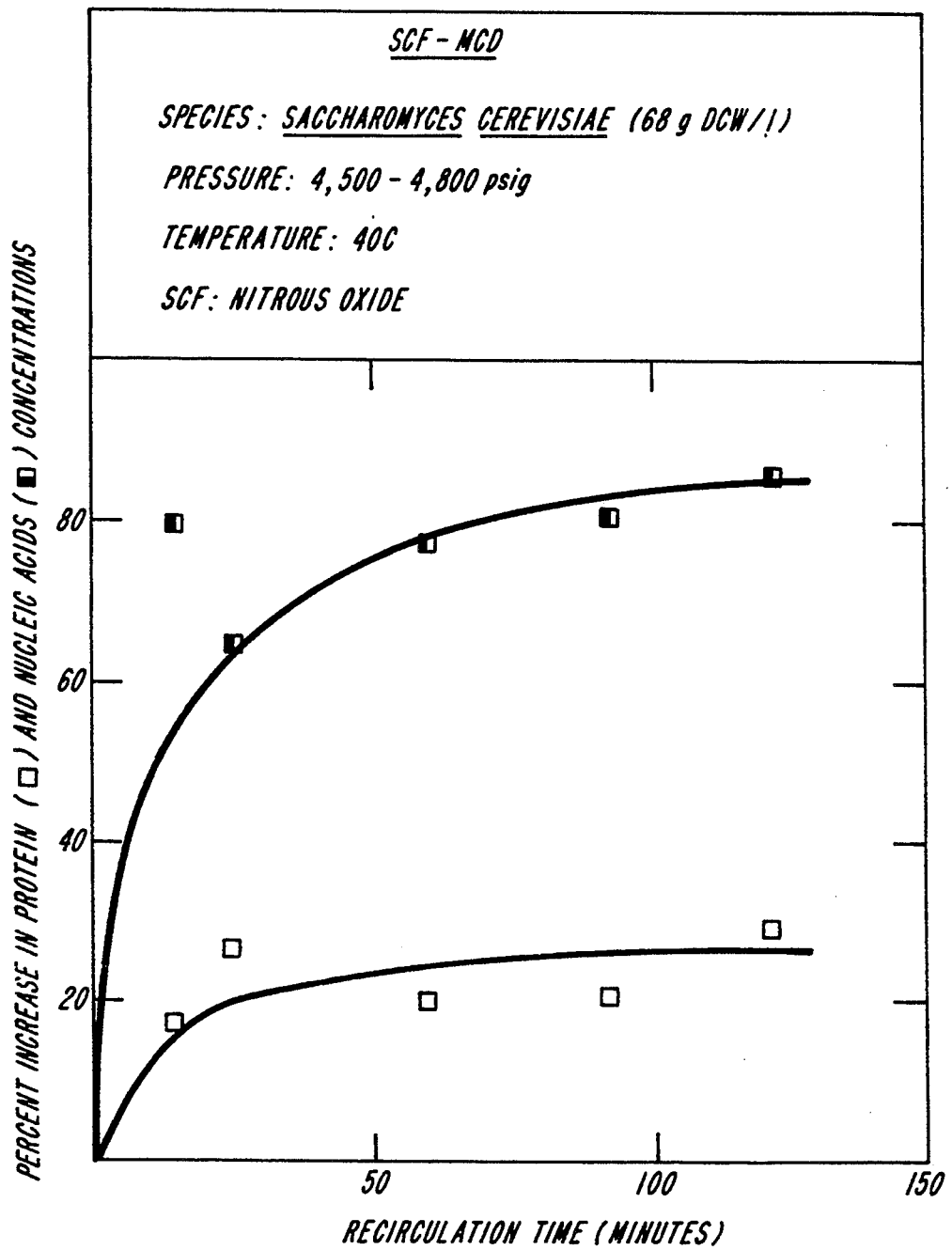
FIG. 12 is a graph illustrating the effect of exposure or recirculation time on the microbial cell disruption of Saccharomyces cerevisiae.

The effect of recirculation or exposure time on the supercritical microbial disruption of *B. subtilis* using $N_2O$ was tested. Temperature and pressure were fixed at 40° C. and about 5000 psig respectively. Recirculation time was varied from 21 minutes to 122 minutes. The relationship between recirculation time and nucleic acids and protein recovery was positive, and almost linear (FIG. 11). Nucleic acids recovery increased from 21.4% at 21 minutes to 70.7% at 122 minutes. Protein recovery increased from 0% at 21 minutes to 41.3% at 122 minutes.

EXAMPLE 7

The effect of recirculation or exposure time on the supercritical microbial disruption of Baker's yeast using $N_2O$ was tested. Temperature and pressure were fixed at 40° C. and about 4700 psig respectively. Recirculation time was varied from about 15 minutes to 122 minutes. The relationship between recirculation time and nucleic acids and protein recovery was asymptotic, with a maximum recovery beginning to level off at about 50 minutes. The nucleic acids recovery increased from 82% at 15 minutes to about 90% at about 122 minutes. The protein recovery increased from 17% at 15 minutes to 28.9% at 122 minutes.

The need for longer recirculation time for *E. coli* and *B. subtilis* may result because mixing may be more efficient in contacting and saturating a single large cell (Baker's yeast) than in saturating an equivalent volume of smaller ones (*E. coli* and *B. subtilis*). The mass transfer limiting step may be diffusion of the solvent through the aqueous phase and into the outer membrane of the cell wall.

EXAMPLE 8

The effect of cell concentration on supercritical microbial disruption of *E. coli* using $N_2O$ was tested. Cell suspensions were prepared in continuous fermenters and were concentrated by some combination of sedimentation, centrifugation and dewatering. To achieve desired cell concentrations, the microbial cell slurries were resuspended and buffered with the same pH, ionic composition (major ions) and molarity as the original growth medium to prevent osmotic lysis due to swelling or osmotic dehydration. Experiments were run at a fixed temperature of 40° C., fixed recirculation time of 25 minutes and a fixed pressure of about 1300 psig.

Figure 13:
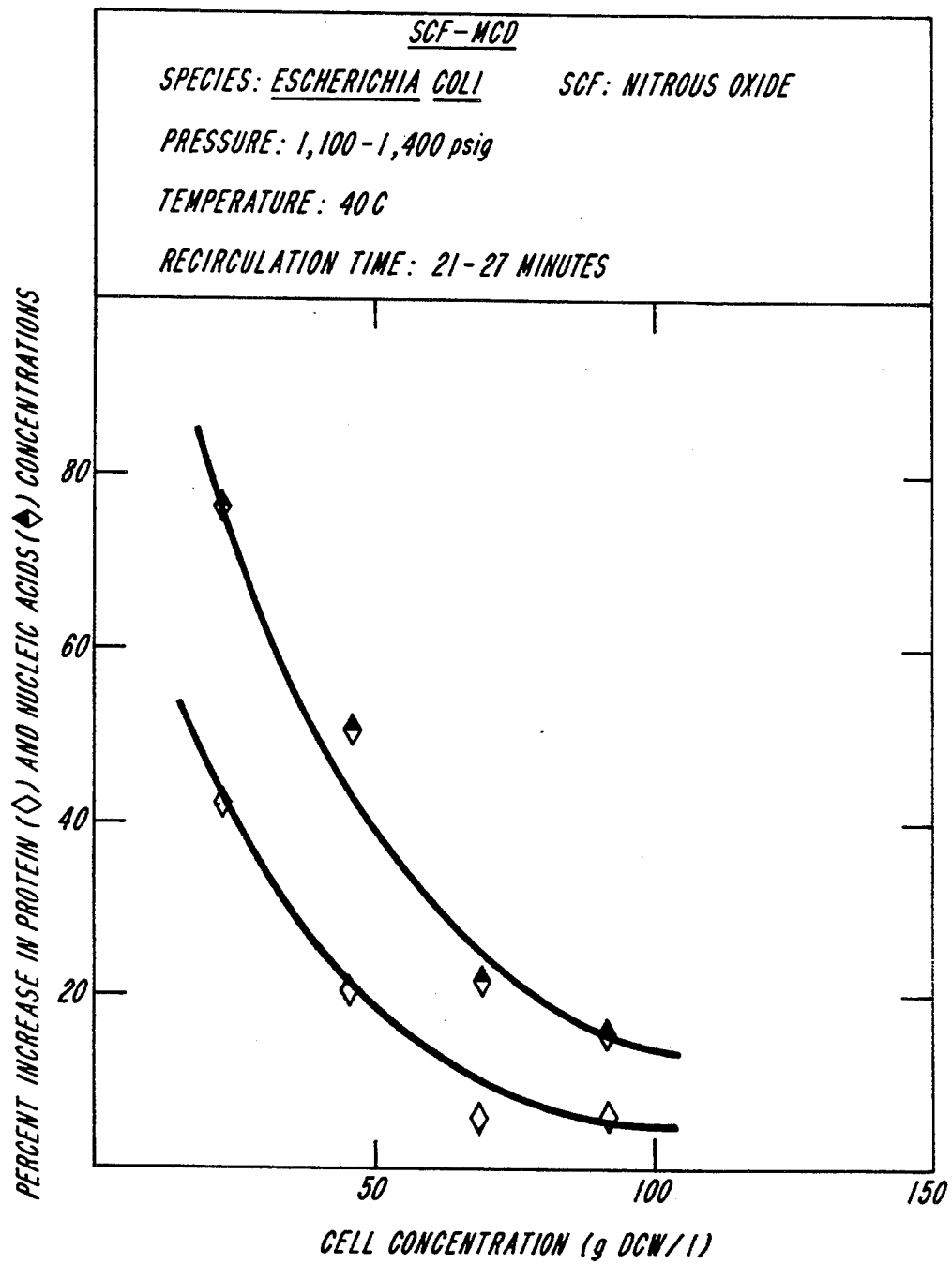
FIG. 13 is a graph illustrating the effect of cell concentration on the microbial cell disruption of E. coli.

Microbial cell disruption efficiency, as measured by percentage change in protein and nucleic acids concentration, decreased rapidly as cell concentration increased (FIG. 13). Recovery of nucleic acids decreased from a high of 76.3% at 22.9 grams DCW/l to a low of 15.9% at 91.7 grams DCW/l. Likewise, recovered protein decreased from a high of 42.7% at 22.9 DCW/1 to a low of 6.5% at 91.7 DCW/1.

EXAMPLE 9

Figure 14:
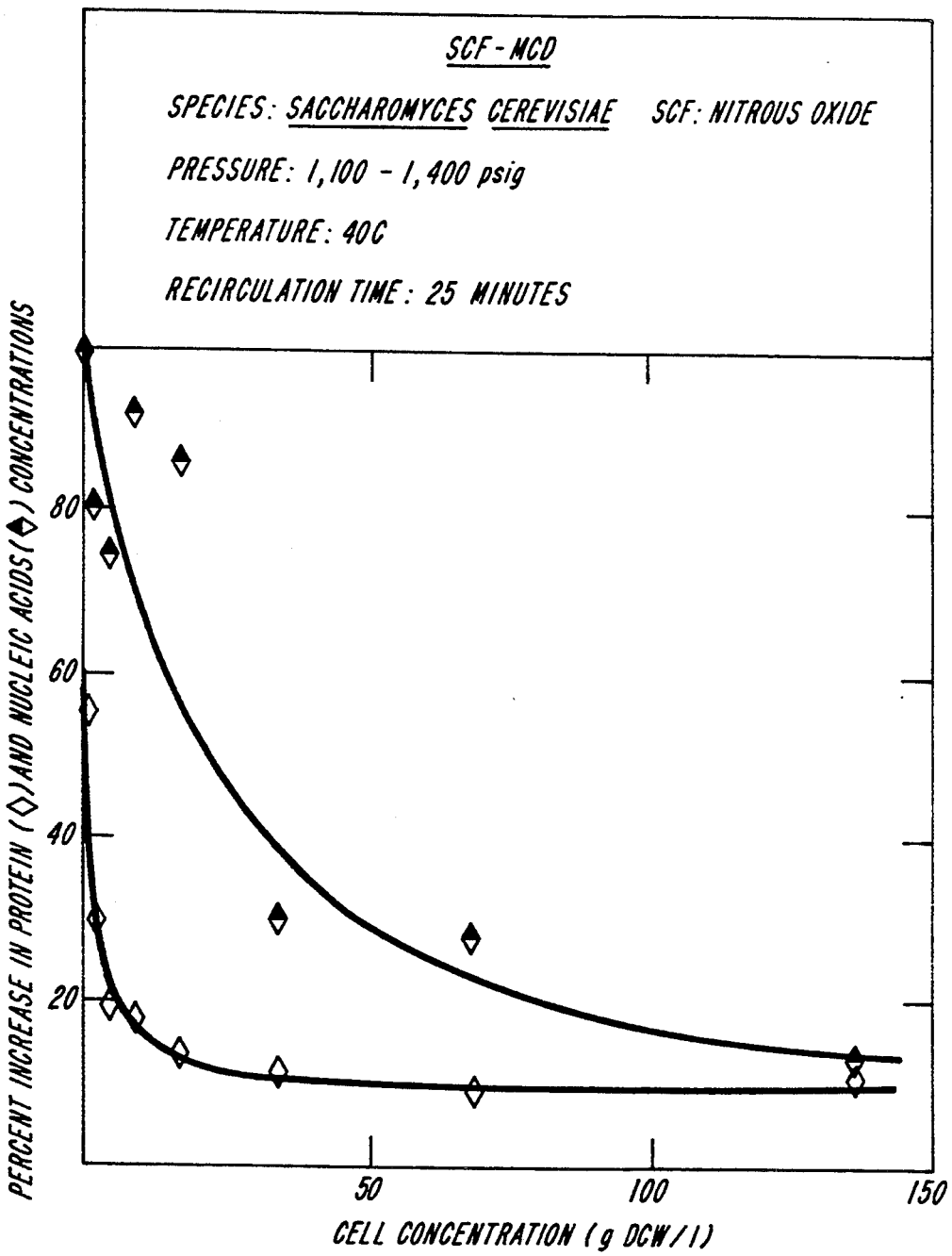
FIG. 14 is a graph illustrating the effect of cell concentration on the microbial cell disruption of Saccharomyces cerevisiae.

The effect of cell concentration on supercritical microbial disruption of Baker's yeast using $N_2O$ was tested. The preparation of the cell suspensions and the conditions for the experiments were as described above in connection with Example 8. The nucleic acids recovery decayed quickly from highs approaching 100% at cell concentrations of 1.1 gram DCW/1 to lows of about 10% at 150 grams DCW/1 (FIG. 14). Protein recovery also decreased rapidly from a high of 55.5% at cell concentrations of 1.1 gram DCW/1 to about 10% at 150 gram DCW/1.

The cell concentration experiments on *E. coli* and Baker's yeast were conducted under moderate conditions (relatively low pressures and short recirculation times) in order to accentuate any effect of cell concentration. It is anticipated that increased pressures and recirculation times and/or more efficient mixing would reduce the levels of decay characteristic of examples 8 and 9.

EXAMPLE 10

The effect of temperature on supercritical microbial disruption of E. coli at a concentration of 39 grams DCW/1 using $N_2O$ was tested. Pressure was fixed about about 4900 psig. One set of experiments was run at 25 minutes recirculation time and another set was run at 125 minutes recirculation time. In each set of experiments, temperature was either just below critical temperature or just above the critical temperature of $N_2O$ which is 36.4° C.

The change in temperature from just below critical temperature to just above critical temperature resulted in an extraordinary and surprising increase in the yield of nucleic acids, while little or no effect on the yield of protein resulted (FIG. 15).

It should be noted that the yield for both nucleic acids and protein at 40° C., At 4900 psig and at a recirculation time of 25 minutes differed greatly from that reported in example 1 above. This may be due to the cell culture and harvest condition differences. In the examples above, cells were harvested during log-phase growth, gravity sedimented at 4° C. overnight, centrifuged and then used. Here, cells were obtained 14 hours into fermentation as the cells approached their stationary phase and then stored at 4° C. for a week before harvesting and centrifugation. It is believed that for a maximum yield, log-phase cells should be employed.

EXAMPLE 11

The effect of temperature on the supercritical microbial disruption of *B. subtilis* using $N_2O$ was tested. The *B. subtilis* were at 62 grams DCW per liter. The pressure was fixed at about 4700 psig. and the recirculation time was fixed at 60 minutes. As shown in FIG. 16, recovery of both nucleic acids and protein increased dramatically when changing the temperature from just below critical temperature to just above critical temperature.

EXAMPLE 12

The effect of temperature on supercritical microbial disruption of Baker's yeast using $N_2O$ was tested. Pressure was fixed at about 1100 psig and recirculation time was fixed at 25 minutes. Temperature was varied from 20° C. to 70° C.

Figure 17:
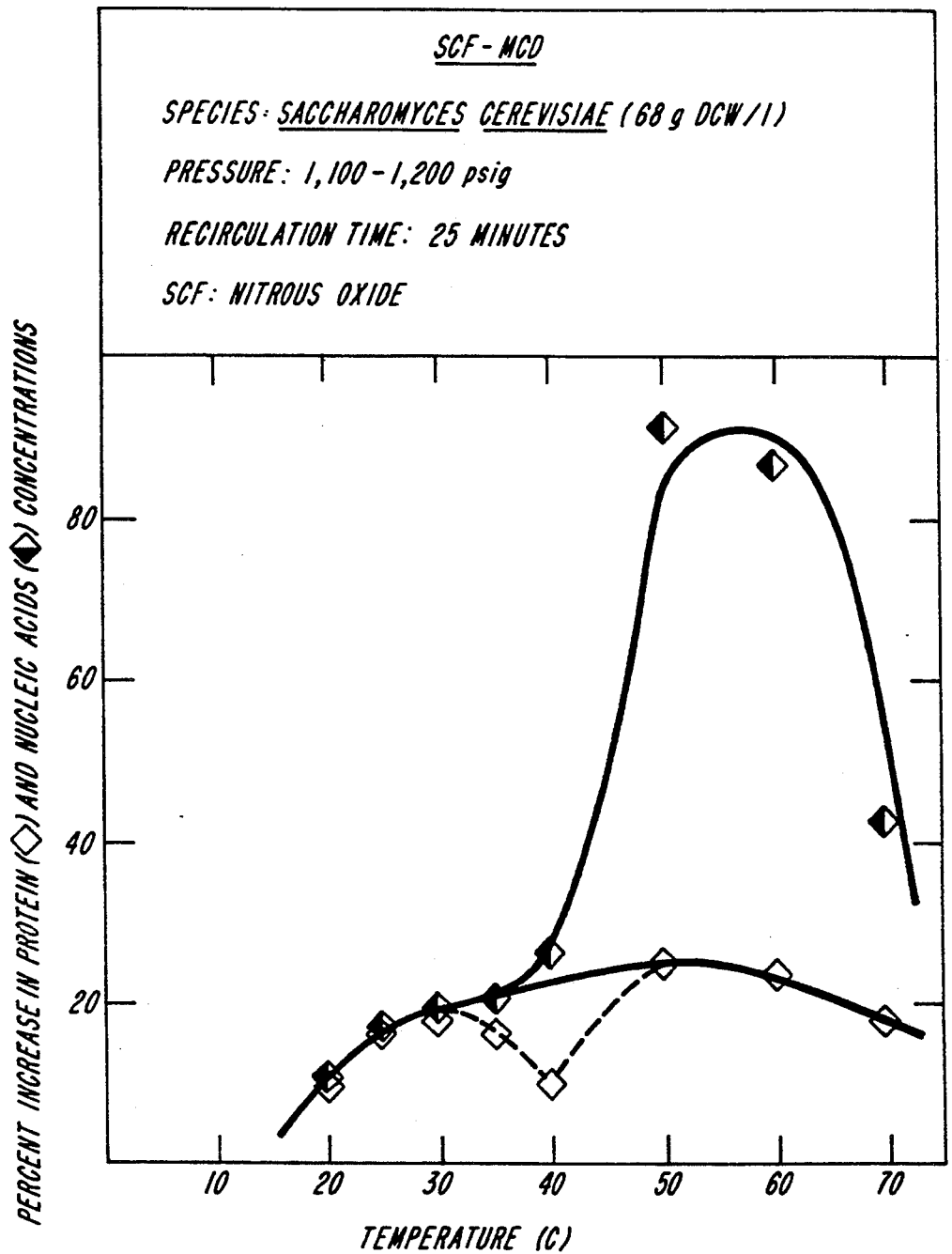
FIG. 17 is a graph illustrating the effect of temperature on the microbial cell disruption of Saccharomyces cerevisiae using $N_2O$.

Nucleic acids and protein recoveries at temperatures below critical temperazure were about equal and increased gradually from 8.7% at 20° C. to about 20% at 35° C. Thereafter, there was a dramatic increase in the nucleic acids recovered, while the percentage of protein recovered increased only slightly with further increases in temperature (FIG. 17). Nucleic acids recovery peaked at 94.4% at a temperature of about 50° C.

EXAMPLE 13

The effect of temperature on supercritical microbial disruption of Baker's yeast using $CO_2$, with a critical temperature of 31.0° C., was also tested. Pressure, recirculation time, and temperature all were varied.

The recovery of nucleic acids increased more rapidly than the recovery of proteins as critical temperature was reached (FIG. 18). Below critical temperature, the amount of nucleic acids recovery and protein recovery was about equal. However, at just 1° above critical temperature, the amount of nucleic acids recovered about doubled while the amount of protein recovered decreased slightly. These results suggest that the efficacy with which the cytoplasmic membrane is disrupted increases rapidly with temperature after the attainment of supercritical temperature.

EXAMPLE 14

The effect of temperature on the supercritical microbial disruption of Baker's yeast using ethylene, with a critical temperature of 9.2° C., was tested. Pressure and temperature were fixed at 1650 psig and about 2 hours respectively. Temperature was set at either 6° C. or 22° C. As shown in FIG. 19, the recovery of both nucleic acids and of protein greatly increased once ethylene's critical temperature of 9.2° C. was surpassed.

It is intended that all matter contained in the above description or shown in the accompanying drawings shall be interpreted in an illustrative and not a limiting sense.

What we claim is:

1. A method for collecting proteins or nucleic acids from intact prokaryotes comprising,
    combining a solvent with the prokaryotes to form a combination, the solvent having a critical pressure and also having a critical temperature between 0° C. and 100° C.,
    subjecting the combination to near critical pressure or higher while maintaining the combination at or near critical temperature,
    suddenly releasing said pressure to cause a pressure drop, and
    collecting any protein or nucleic acids that have been released from the prokaryotes.

2. A method as claimed in claim 1 further comprising first carrying out the steps of claim 1 while maintaining the combination at just below critical temperature and then repeating said steps while maintaining said combination just above critical temperature.

3. A method for collecting proteins or nucleic acids from intact eukaryotes comprising,
    combining a nonacidic solvent with the eukaryotes to form a combination, the solvent having a critical pressure and also having a critical temperature between 0° C. and 100° C.,
    subjecting the combination to near critical pressure or higher while maintaining the combination at or near critical temperature,
    suddenly releasing the pressure to cause a pressure drop, and
    collecting any proteins or nucleic acids that have been released from the eukaryote from the phase containing disrupted prokaryotes.

4. A method as claimed in claim 3 wherein the combination is maintained just below critical temperature.

5. A method as claimed in claim 3 further comprising, first carrying out the steps in claim 3 while maintaining the combination at just below critical temperature, and then repeating said steps while maintaining the combination at just above critical temperature.

6. A method for selectively collecting protein from intact *procaryotic* cells comprising, combining a solvent with the procaryotic cells to form a combination, said solvent having a critical temperature and a critical pressure, maintaining the combination under conditions sufficient to cause permeabitization of the cell wall but not the cytoplasmic membrane, said conditions including subjecting the combination to pressures at or above the critical pressure of the solvent, suddenly releasing the pressure to cause a pressure drop, and collecting protein that has been released from the procaryotic cells.

7. A method for collecting proteins or nucleic acids from intact prokaryotes comprising the steps:

combining a solvent with one or more prokaryotes to form a combination, said solvent having a critical pressure and having a critical temperature between 0° C. and 100° C.;

subjecting said combination to near critical pressure or higher while maintaining said combination at a temperature which is near, just below said critical temperature;

suddenly releasing said pressure to cause a pressure drop, and collecting proteins or nucleic acids released from said prokaryotes.

8. A method as claimed in claim 7 further comprising the steps:

following the step of collecting protein or nucleic acids released from the prokaryotes, subjecting said combination to near critical pressure or higher while maintaining said combination just above critical temperature, suddenly releasing said pressure to cause a pressure drop, and collecting proteins or nucleic acids released from said prokaryotes.

9. A method for collecting proteins or nucleic acids from intact eukaryotes comprising, the steps:

combining a nonacid solvent with one or more eukaryotes to form a combination, the solvent having a critical pressure and also having a critical temperature between 0° C. and 100° C., subjecting said combination to near critical pressure or higher while maintaining the combination at a temperature which is at, near, or just below said critical temperature, suddenly releasing the pressure to cause a pressure drop, and collecting any proteins or nucleic acids that have been released from the eukaryotes.

10. A method as claimed in claim 9 further comprising the steps:

following the step of collecting proteins or nucleic acids released from the eukaryotes, subjecting said combination to near critical pressure or higher while maintaining said combination just above critical temperature, suddenly releasing said pressure to cause a pressure drop, and collecting proteins or nucleic acids released from said eukaryotes.

* * * * *